United States Patent
Lee et al.

(10) Patent No.: US 9,700,871 B2
(45) Date of Patent: Jul. 11, 2017

(54) METHOD FOR PREPARING SUPER ABSORBENT RESIN

(71) Applicant: LG Chem, Ltd., Seoul (KR)

(72) Inventors: Seung-Mo Lee, Daejeon (KR); Young-Sam Kim, Daejeon (KR); Kyoung-Shil Oh, Daejeon (KR); Young-In Yang, Daejeon (KR); Ye-Hon Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 14/907,470

(22) PCT Filed: Dec. 3, 2014

(86) PCT No.: PCT/KR2014/011788
§ 371 (c)(1),
(2) Date: Jan. 25, 2016

(87) PCT Pub. No.: WO2015/084059
PCT Pub. Date: Jun. 11, 2015

(65) Prior Publication Data
US 2016/0271584 A1 Sep. 22, 2016

(30) Foreign Application Priority Data

Dec. 3, 2013 (KR) .................. 10-2013-0149440
May 30, 2014 (KR) .................. 10-2014-0066046
Dec. 3, 2014 (KR) .................. 10-2014-0172232

(51) Int. Cl.
| | | |
|---|---|---|
| C08F 2/46 | (2006.01) | |
| C08F 2/50 | (2006.01) | |
| C08G 61/04 | (2006.01) | |
| B01J 20/26 | (2006.01) | |
| A61L 15/60 | (2006.01) | |
| C08F 20/06 | (2006.01) | |
| C08J 3/075 | (2006.01) | |
| C08F 2/48 | (2006.01) | |
| C08J 3/24 | (2006.01) | |
| B01J 20/30 | (2006.01) | |
| C08F 220/06 | (2006.01) | |
| C08J 3/12 | (2006.01) | |

(52) U.S. Cl.
CPC .......... B01J 20/267 (2013.01); A61L 15/60 (2013.01); B01J 20/3021 (2013.01); B01J 20/3085 (2013.01); C08F 2/48 (2013.01); C08F 20/06 (2013.01); C08F 220/06 (2013.01); C08J 3/075 (2013.01); C08J 3/12 (2013.01); C08J 3/245 (2013.01); C08J 2333/02 (2013.01)

(58) Field of Classification Search
CPC .. B01J 20/267; B01J 20/3021; B01J 20/3085; C08J 2333/02; C08J 3/245; C08J 3/12; C08J 3/075; C08F 220/06; C08F 2222/1013; C08F 2222/1026; C08F 2/48; C08F 20/06; A61L 15/60
USPC ........... 522/77, 74, 71, 6, 189, 184, 1; 520/1
See application file for complete search history.

(56) References Cited

U.S. PATENT DOCUMENTS

| | | | |
|---|---|---|---|
| 5,973,042 A | 10/1999 | Yoshinaga et al. | |
| 2003/0144386 A1 | 7/2003 | Pakusch et al. | |
| 2009/0204087 A1 | 8/2009 | Herfert et al. | |
| 2014/0051813 A1* | 2/2014 | Won ..................... | C08J 3/245 525/384 |
| 2014/0058048 A1* | 2/2014 | Won ..................... | B01J 20/267 525/384 |
| 2015/0094427 A1* | 4/2015 | Lee ..................... | C08J 3/24 525/194 |
| 2015/0259522 A1* | 9/2015 | Lee ..................... | B01J 20/261 524/522 |
| 2015/0315321 A1* | 11/2015 | Won ..................... | A61L 15/22 525/328.8 |
| 2016/0184799 A1* | 6/2016 | Lee ..................... | C08F 20/10 525/296 |
| 2016/0214082 A1* | 7/2016 | Lee ..................... | B01J 20/28026 |
| 2016/0311985 A1* | 10/2016 | Jung ..................... | C08J 3/245 |

FOREIGN PATENT DOCUMENTS

| | | |
|---|---|---|
| CN | 1098727 A | 2/1995 |
| JP | 2004002145 A | 1/2004 |
| JP | 2009057496 A | 3/2009 |
| JP | 2010501698 A | 1/2010 |
| JP | 2010253283 A | 11/2010 |

(Continued)

OTHER PUBLICATIONS

International Search Report for Application No. PCT/KR2014/011788 dated Mar. 10, 2015.

(Continued)

*Primary Examiner* — Jessica E Whiteley
(74) *Attorney, Agent, or Firm* — Lerner, David, Littenberg, Krumholz & Mentlik, LLP

(57) ABSTRACT

Disclosed is a method of preparing a superabsorbent polymer, including a) subjecting a monomer composition composed of a water-soluble ethylenic unsaturated monomer and a polymerization initiator to thermal polymerization or photopolymerization, thus preparing a hydrous gel polymer, b) drying the hydrous gel polymer, c) grinding the dried hydrous gel polymer, d) adding the ground hydrous gel polymer with particles having i) a BET specific surface area of 300 to 1500 m²/g and ii) a porosity of 50% or more and with a surface crosslinking agent, and e) performing a surface crosslinking reaction.

22 Claims, No Drawings

(56) References Cited

FOREIGN PATENT DOCUMENTS

| | | | |
|---|---|---|---|
| JP | 2012052080 | A | 3/2012 |
| KR | 19990028909 | | 4/1999 |
| KR | 20120059169 | A | 6/2012 |
| KR | 20120081113 | A | 7/2012 |
| WO | 2005120594 | A1 | 12/2005 |
| WO | 2011001036 | A1 | 1/2011 |
| WO | 2012070845 | A2 | 5/2012 |
| WO | 2013087926 | A1 | 6/2013 |

OTHER PUBLICATIONS

Extended Search Report from European Application No. 14867984.8, dated Sep. 12, 2016.

* cited by examiner

METHOD FOR PREPARING SUPER ABSORBENT RESIN

CROSS-REFERENCE TO RELATED APPLICATION

This application is a national phase entry under 35 U.S.C. §371 of International Application No. PCT/KR2014/011788, filed Dec. 3, 2014, which claims priority to Korean Patent Application No. 10-2013-0149440, filed Dec. 3, 2013, Korean Patent Application No. 10-2014-0066046, filed May 30, 2014 and Korean Patent Application No. 10-2014-0172232, filed Dec. 3, 2014, the disclosures of which are incorporated herein by reference.

TECHNICAL FIELD

The present invention relates to a method of preparing a superabsorbent polymer and, more particularly, to a method of preparing a superabsorbent polymer having superhydrophobic microparticles introduced thereto.

BACKGROUND ART

Superabsorbent polymers (SAPs) are synthetic polymers that are able to absorb about 500 to 1000 times their own weight in water. Such superabsorbent polymers have begun to be used in real-world applications for sanitary items, and are currently being widely utilized not only in hygiene products, such as disposable baby diapers, sanitary pads and the like, but also in gardening soil repair agents, water stop materials for civil construction, seeding sheets, freshness retaining agents in the field of food distribution, and fomentation materials.

In the preparation of the superabsorbent polymer, water, which is the polymerization medium, is used in various applications, including facilitating the dispersion of the crosslinking agent during the surface crosslinking process, etc. Also, residual moisture in the final product functions as an anti-static agent and a plasticizer for resin, and plays a role in suppressing the generation of very fine superabsorbent polymer dust in the course of application, and additionally preventing the grinding of the superabsorbent polymer particles. Generally, however, when even a small amount of water is added to the superabsorbent polymer, the surface stickiness of the polymer may be increased by the water absorbed thereto, and irreversible agglomeration of the superabsorbent polymer particles may take place. This increase in stickiness and agglomeration may result in poor processability, such as a high burden on the preparation and application processes, consequently increasing the particle size of the superabsorbent polymer, deteriorating the properties thereof, and decreasing productivity. Superabsorbent polymers have been mainly studied to date for polymerization processes and improved absorption performance, and for surface crosslinkage to realize surface properties thereof or increased absorption under pressure, and research leading to changes in the surface properties of superabsorbent polymers has been carried out to increase transmittance or to prevent caking when the superabsorbent polymers are stored.

In this regard, Korean Patent Application Publication No. 2012-0081113 discloses a method of preparing an absorbent polymer containing water-insoluble inorganic particles.

However, this conventional technique is problematic because the surface stickiness of the superabsorbent polymer increases with an increase in moisture content on the surface thereof, undesirably resulting in agglomeration, poor processability, and low productivity, as in the above case. Hence, there is a requirement to develop a superabsorbent polymer that may satisfy both high moisture content and high processability.

DISCLOSURE

Technical Problem

The present invention has been made keeping in mind the above problems encountered in the related art, and an object of the present invention is to provide a method of preparing a superabsorbent polymer having porous superhydrophobic microparticles introduced thereto, in which the surface of a superabsorbent polymer is modified to be hydrophobic to thus decrease stickiness and agglomeration upon the absorption of water, thereby increasing processability and thus reducing processing loads, facilitating the control of particle size and properties thereof, and satisfying both high moisture content and high processability, thereby minimizing the deterioration of properties due to resin breakage in application processes.

Technical Solution

In order to accomplish the above object, the present invention provides a method of preparing a superabsorbent polymer, comprising: a) subjecting a monomer composition comprising a water-soluble ethylenic unsaturated monomer and a polymerization initiator to thermal polymerization or photopolymerization, thus preparing a hydrous gel polymer; b) drying the hydrous gel polymer; c) grinding the dried hydrous gel polymer; d) adding the ground hydrous gel polymer with particles having i) a BET specific surface area of 300 to 1500 $m^2/g$ and ii) a porosity of 50% or more and with a surface crosslinking agent; and e) performing a surface crosslinking reaction.

Advantageous Effects

In the method of preparing a superabsorbent polymer according to the present invention, the surface of a superabsorbent polymer is modified to be hydrophobic to thus decrease stickiness and agglomeration upon the absorption of water, thereby increasing processability and thus reducing processing loads, facilitating the control of particle size and properties thereof, and satisfying both high moisture content and high processability, thereby minimizing the deterioration of properties due to resin breakage in application processes.

BEST MODE

Hereinafter, a detailed description will be given of the present invention.

According to the present invention, a method of preparing a superabsorbent polymer includes a) subjecting a monomer composition comprising a water-soluble ethylenic unsaturated monomer and a polymerization initiator to thermal polymerization or photopolymerization, thus preparing a hydrous gel polymer, b) drying the hydrous gel polymer, c) grinding the dried hydrous gel polymer, d) adding the ground hydrous gel polymer with particles having i) a BET specific surface area of 300 to 1500 $m^2/g$ and ii) a porosity of 50% or more and with a surface crosslinking agent, and e) performing a surface crosslinking reaction.

Specifically, the method of preparing the superabsorbent polymer according to the present invention includes a) subjecting a monomer composition comprising a water-soluble ethylenic unsaturated monomer and a polymerization initiator to thermal polymerization or photopolymerization, thus preparing a hydrous gel polymer.

In the preparation of the superabsorbent polymer according to the present invention, the above polymer may be prepared by steps and methods typically used in the art. Particularly, upon the preparation of the superabsorbent polymer according to the present invention, the monomer composition includes a polymerization initiator. Depending on the polymerization method, when photopolymerization is performed, a photopolymerization initiator is used, and when thermal polymerization is performed, a thermal polymerization initiator is employed. Even when photopolymerization is conducted, a predetermined amount of heat is generated due to irradiation with UV light and also through the polymerization, which is an exothermic reaction, and thus a thermal polymerization initiator may be additionally used.

In the method of preparing the superabsorbent polymer according to the present invention, the thermal polymerization initiator is not particularly limited, but preferably includes at least one selected from the group consisting of a persulfate-based initiator, an azo-based initiator, hydrogen peroxide, and ascorbic acid. Specifically, examples of the persulfate-based initiator may include sodium persulfate ($Na_2S_2O_8$), potassium persulfate ($K_2S_2O_8$), and ammonium persulfate (($NH_4$)$_2S_2O_8$), and examples of the azo-based initiator may include 2,2-azobis(2-amidinopropane)dihydrochloride, 2,2-azobis-(N,N-dimethylene)isobutyramidine dihydrochloride, 2-(carbamoylazo)isobutyronitrile, 2,2-azobis[2-(2-imidazolin-2-yl)propane]dihydrochloride, and 4,4-azobis-(4-cyanovaleric acid).

In the method of preparing the superabsorbent polymer according to the present invention, the photopolymerization initiator is not particularly limited, but preferably includes at least one selected from the group consisting of benzoin ether, dialkyl acetophenone, hydroxyl alkyl ketone, phenyl glyoxylate, benzyl dimethyl ketal, acyl phosphine, and α-aminoketone. Specifically, acyl phosphine may be exemplified by commercially available Lucirin TPO, that is, 2,4,6-trimethyl-benzoyl-trimethyl phosphine oxide.

In the method of preparing the superabsorbent polymer according to the present invention, the water-soluble ethylenic unsaturated monomer is not particularly limited, so long as it is a monomer typically used to synthesize a superabsorbent polymer, and preferably includes any one or more selected from the group consisting of an anionic monomer and salts thereof, a nonionic hydrophilic monomer, and an amino group-containing unsaturated monomer and quaternary salts thereof. Particularly useful is at least one selected from the group consisting of anionic monomers and salts thereof, such as acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid, and 2-(meth)acrylamide-2-methylpropane sulfonic acid; non-ionic hydrophilic monomers, such as (meth)acrylamide, N-substituted (meth)acrylate, 2-hydroxyethyl(meth)acrylate, 2-hydroxypropyl(meth)acrylate, methoxypolyethyleneglycol (meth)acrylate, and polyethyleneglycol (meth) acrylate; and amino group-containing unsaturated monomers and quaternary salts thereof, such as (N,N)-dimethylaminoethyl (meth)acrylate, and (N,N)-dimethylaminopropyl (meth)acrylamide. More preferably, acrylic acid or salts thereof are used. When acrylic acid or salts thereof are used as the monomer, a superabsorbent polymer having high absorbability may be advantageously obtained.

In the method of preparing the superabsorbent polymer according to the present invention, the monomer composition may include a predetermined amount of a polymer or resin powder having a particle size of less than 150 μm, corresponding to dust of the prepared superabsorbent polymer powder for the sake of recycling. Specifically, the polymer or resin powder having a particle size of less than 150 μm may be added before the initiation of the polymerization of the monomer composition, or in the early, middle or late stages, after the initiation of polymerization. As such, the amount thereof that is added is not limited, but is preferably set to 1 to 10 parts by weight based on 100 parts by weight of the monomer contained in the monomer composition, in order to prevent the properties of the final superabsorbent polymer from deteriorating.

In the method of preparing the superabsorbent polymer according to the present invention, the concentration of the water-soluble ethylenic unsaturated monomer of the monomer composition may be set appropriately in consideration of the polymerization time and the reaction conditions, but is preferably set to 40 to 55 wt %. If the concentration of the water-soluble ethylenic unsaturated monomer is less than 40 wt %, economic benefits are negated. On the other hand, if the concentration thereof exceeds 55 wt %, the grinding efficiency of the hydrous gel polymer may decrease in the grinding process.

Whether the hydrous gel polymer is prepared from the monomer composition using thermal polymerization or photopolymerization is not limited, so long as it is typically used. Specifically, polymerization methods are largely classified into thermal polymerization and photopolymerization depending on the polymerization energy source. Typically, thermal polymerization is conducted using a reactor with a stirring shaft, such as a kneader, and photopolymerization is implemented using a reactor with a moving conveyor belt. However, the above polymerization methods are merely illustrative, and the present invention is not limited to those polymerization methods.

For example, hot air is fed to a reactor with a stirring shaft, such as a kneader, or the reactor is heated, so that thermal polymerization is carried out, yielding a hydrous gel polymer, which is then discharged at a size ranging from ones of mm to ones of cm through the outlet of the reactor, depending on the shape of the stirring shaft of the reactor. Specifically, the size of the hydrous gel polymer may vary depending on the concentration of the supplied monomer composition and the rate at which it is supplied, and typically a hydrous gel polymer having a particle size of 2 to 50 mm may be obtained.

Also, when photopolymerization is carried out using a reactor with a moving conveyor belt, a hydrous gel polymer in the form of a sheet having the same width as the belt may result. As such, the thickness of the polymer sheet may vary depending on the concentration of the supplied monomer composition and the rate at which it is supplied, but the monomer composition is preferably supplied so as to form a polymer sheet having a thickness ranging from 0.5 to 5 cm. In the case where the monomer composition is supplied in such an amount that a very thin polymer sheet is formed, production efficiency may undesirably decrease. On the other hand, if the thickness of the polymer sheet is greater than 5 cm, polymerization may not be uniformly carried out throughout the sheet, because it is too thick.

Next, the method of preparing the superabsorbent polymer according to the present invention includes b) drying the hydrous gel polymer.

The hydrous gel polymer obtained in a) typically has a moisture content ranging from 30 to 60 wt %. As used herein, the term "moisture content" refers to the amount of moisture based on the total weight of the hydrous gel polymer, that is, a value obtained by subtracting the weight of the dried polymer from the weight of the hydrous gel polymer. Specifically, it is defined as a value calculated by measuring the weight reduction due to the evaporation of moisture from the polymer while the polymer is dried at a high temperature via IR heating. Here, the drying is performed in such a manner that the temperature is increased from room temperature to 180° C. and then maintained at 180° C., and the total drying time is set to 20 min, including the 5 min required to increase the temperature.

As used herein, the term "drying temperature" refers to the temperature of the heat medium used for the drying process or the temperature of the drying reactor, including the heat medium and the polymer, in the drying process. The drying step is preferably performed at a drying temperature of 150 to 250° C., and more preferably 160 to 200° C.

If the drying temperature is lower than 150° C., the drying time may become excessively long, and the properties of the final superabsorbent polymer may deteriorate. On the other hand, if the drying temperature is higher than 250° C., only the surface of the polymer may be excessively dried, and thereby dust may be generated in the subsequent grinding process, and the properties of the final superabsorbent polymer may deteriorate. The drying time is not limited, but may be set to 20 to 90 min taking into account the processing efficiency.

Additionally, the drying process is not limited so long as it is typically used to dry a hydrous gel polymer. Specific examples thereof may include the supply of hot air, IR irradiation, microwave irradiation, and UV irradiation. The polymer after the drying process may have a moisture content of 0.1 to 10 wt %.

Meanwhile, the method of preparing the superabsorbent polymer according to the present invention may further include a simple grinding process before the drying process, as necessary, in order to increase the drying efficiency. The simple grinding process before the drying process is conducted so that the particle size of the hydrous gel polymer ranges from 1 to 15 mm. Grinding the polymer until the particle size is less than 1 mm is technically difficult due to the high moisture content of the hydrous gel polymer, and furthermore, the ground particles may agglomerate. On the other hand, if the polymer is ground to a particle size larger than 15 mm, the effect of increasing the drying efficiency via the grinding process may become insignificant.

In the simple grinding process before the drying process, any grinder may be used without limitation. The specific example thereof may include, but is not limited to, any one selected from the group consisting of a vertical pulverizer, a turbo cutter, a turbo grinder, a rotary cutter mill, a cutter mill, a disc mill, a shred crusher, a crusher, a chopper, and a disc cutter.

When the grinding process is performed to increase the drying efficiency before the drying process in this way, the polymer, which has high moisture content, may stick to the surface of the grinder. Thus, in order to increase the grinding efficiency of the hydrous gel polymer before the drying process, an additive that is able to prevent stickiness during grinding may also be used. The specific kind of additive that may be found useful is not limited. Examples thereof may include, but are not limited to, a powder agglomeration inhibitor, such as steam, water, a surfactant, clay or silica as an inorganic powder; a thermal polymerization initiator, such as a persulfate-based initiator, an azo-based initiator, hydrogen peroxide, and ascorbic acid; and a crosslinking agent, such as an epoxy-based crosslinking agent, a diol-based crosslinking agent, a bifunctional or trifunctional or higher polyfunctional acrylate, and a monofunctional compound having a hydroxyl group.

After the drying process, the method of preparing the superabsorbent polymer according to the present invention includes c) grinding the dried polymer. Thereby, the resulting polymer has a particle size ranging from 150 to 850 µm. In the method of preparing the superabsorbent polymer according to the present invention, the grinder used to obtain this particle size may include, but is not limited to, a pin mill, a hammer mill, a screw mill, a roll mill, a disc mill, or a jog mill.

Next, the method of preparing the superabsorbent polymer according to the present invention includes d) adding the ground hydrous gel polymer with particles having i) a BET specific surface area of 300 to 1500 $m^2/g$ and ii) a porosity of 50% or more and with a surface crosslinking agent.

Typically, a superabsorbent polymer has a hydrophilic surface, and irreversible agglomeration thereof may occur due to capillary force, hydrogen bonding, inter-particular diffusion, or inter-particular van der Waals force, attributable to the presence of water between the particles upon drying after water absorption. Hence, water is essentially used in the course of polymerization and surface crosslinking of the superabsorbent polymer, and thereby agglomeration occurs, thus increasing the internal load, ultimately incurring damage to the system. Furthermore, since the agglomerated superabsorbent polymer has a large particle size, which is unsuitable for use in practice, a disintegration process has to be implemented in order to suitably decrease the large particle size. Also, strong force is applied during the disintegration process, undesirably deteriorating the properties of the superabsorbent polymer, due to attrition of the superabsorbent polymer.

In order to solve these problems, attempts have been made to introduce a variety of microparticles, which function to prevent the direct agglomeration of the polymer particles, to the surface of the superabsorbent polymer. In the case where the microparticles are added in an excessive amount, agglomeration may be prevented, but the absorption performance of the superabsorbent polymer may decrease.

To solve this problem, the microparticles introduced to the superabsorbent polymer according to the present invention have a particle size ranging from 2 nm to 50 µm. Also, the microparticles have a BET specific surface area of 300 to 1500 $m^2/g$, preferably 500 to 1500 $m^2/g$, and more preferably 700 to 1500 $m^2/g$. The microparticles have superhydrophobicity with a water contact angle of 125° or more, preferably 140° or more, and more preferably 145° or more. Furthermore, the microparticles have a porosity of 50% or more, and preferably 90% or more. In the method of preparing the superabsorbent polymer according to the present invention, the use of the microparticles having the properties as described above may decrease the effect of water that is present on the surface of the polymer, and furthermore, the use of porous superhydrophobic microparticles may remarkably reduce agglomeration. Even when a relatively small amount of microparticles is used, permeability may be easily increased, and high water content and retention may be readily ensured.

In the method of preparing the superabsorbent polymer according to the present invention, the material for the microparticles is not limited so long as it has the above properties i) and ii), and examples thereof may include, but are not limited to, inorganic oxides, such as silica ($SiO_2$), alumina, titania ($TiO_2$), carbon, inorganic compounds, organic polymers, ion exchange resins, metals, metal salts, etc.

Also, the microparticles are preferably added in an amount of 0.001 to 1 parts by weight based on 100 parts by weight of the superabsorbent polymer. If the amount of the microparticles is less than the above lower limit, the superabsorbent polymer has insufficient hydrophobicity. On the other hand, if the amount thereof is higher than the upper limit, processability of the polymer may decrease.

Also, the microparticles may be added in a manner in which the microparticles are dispersed in a monomer solution, added to a hydrous gel polymer, and then dry-mixed with primarily dried polymer particles, or are dispersed in water or an organic solvent containing a dissolved surface crosslinking agent upon surface crosslinking and then mixed, or are dry-mixed separately from water or an organic solvent containing a dissolved surface crosslinking agent upon surface crosslinking, or are dry-mixed with a surface crosslinked product, but the present invention is not particularly limited thereto.

In the method of preparing the superabsorbent polymer according to the present invention, the surface crosslinking agent is not limited, so long as it is able to react with the functional group of the polymer. In order to improve the properties of the superabsorbent polymer, the surface crosslinking agent may include at least one selected from the group consisting of a polyhydric alcohol compound, an epoxy compound, a polyamine compound, a haloepoxy compound, a haloepoxy compound condensed product, an oxazoline compound, a mono-, di- or poly-oxazolidinone compound, a cyclic urea compound, a polyhydric metal salt, and an alkylene carbonate compound.

Specifically, the polyhydric alcohol compound may include at least one selected from the group consisting of mono-, di-, tri-, tetra- or poly-ethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

Examples of the epoxy compound may include ethylene glycol diglycidyl ether and glycidol, and the polyamine compound may include at least one selected from the group consisting of ethylene diamine, diethylene triamine, triethylene tetramine, tetraethylene pentamine, pentaethylene hexamine, polyethyleneimine, and polyamide polyamine.

Examples of the haloepoxy compound may include epichlorohydrin, epibromohydrin, and α-methyl epichlorohydrin. The mono-, di- or poly-oxazolidinone compound may be exemplified by 2-oxazolidinone. The alkylene carbonate compound may include ethylene carbonate. These compounds may be used alone or in combination. To increase the efficiency of the surface crosslinking process, the surface crosslinking agent preferably includes at least one polyhydric alcohol compound, and more preferably includes a polyhydric alcohol compound having 2 to 10 carbon atoms.

The amount of the surface crosslinking agent that is added in order to treat the surface of the polymer particles may be appropriately determined depending on the kind of surface crosslinking agent and the reaction conditions, and is set to 0.001 to 5 parts by weight, preferably 0.01 to 3 parts by weight, and more preferably 0.05 to 2 parts by weight, based on 100 parts by weight of the polymer.

If the amount of the surface crosslinking agent is too small, the surface crosslinking reaction does not readily occur. On the other hand, if the amount thereof exceeds 5 parts by weight based on 100 parts by weight of the polymer, the properties of the superabsorbent polymer may be deteriorated due to excessive surface crosslinking reactions.

As such, the manner in which the surface crosslinking agent is added to the polymer is not limited. Specifically, the surface crosslinking agent and the polymer powder may be placed in a reaction bath and mixed, the surface crosslinking agent may be sprayed onto the polymer powder, or the polymer and the crosslinking agent may be continuously supplied and mixed using a reaction bath such as a mixer that operates continuously.

The method of preparing the superabsorbent polymer according to the present invention includes e) performing a surface crosslinking reaction.

In another embodiment of the present invention, the temperature of the polymer itself may be 20 to 80° C. when the surface crosslinking agent is added, so that the temperature is increased to the reaction temperature within 1 to 60 min to perform surface crosslinking in the presence of the surface crosslinking agent. To realize the above temperature of the polymer itself, processes after the drying process, which is carried out at a relatively high temperature, are continuously carried out, and the processing time may be shortened. Alternatively, the polymer may be heated separately if it is difficult to shorten the processing time.

In the method of preparing the superabsorbent polymer according to the present invention, the surface crosslinking agent that is added to the polymer may be heated in order to increase the temperature to the reaction temperature within 1 to 60 min to perform surface crosslinking in the presence of the surface crosslinking agent.

Meanwhile, in the method of preparing the superabsorbent polymer according to the present invention, when the surface crosslinking reaction is carried out after the temperature has been increased to the reaction temperature within 1 to 60 min in order to prepare for surface crosslinking, the efficiency of the surface crosslinking process may be increased. Ultimately, the residual monomer content of the final superabsorbent polymer may be minimized, and a superabsorbent polymer having superior properties may be attained. As such, the temperature of the added surface crosslinking agent is adjusted within the range from 5 to 60° C., and preferably 10 to 40° C. If the temperature of the surface crosslinking agent is lower than 5° C., the heating rate reduction effect for the surface crosslinking reaction due to heating of the surface crosslinking agent may become insignificant. On the other hand, if the temperature of the surface crosslinking agent is higher than 60° C., the surface crosslinking agent may not be uniformly dispersed in the polymer. As used herein, the surface crosslinking reaction temperature may be defined as the overall temperature of the polymer and the surface crosslinking agent that is added for the crosslinking reaction.

The heating member for the surface crosslinking reaction is not limited. Specifically, a heat medium may be supplied, or direct heating may be conducted using electricity, but the present invention is not limited thereto. Specific examples of the heat source may include steam, electricity, UV light, and IR light. Additionally, a heated thermal fluid may be used.

In the method of preparing the superabsorbent polymer according to the present invention, after heating for the crosslinking reaction, the crosslinking reaction is carried out for a period of time ranging from 1 to 60 min, preferably 5 to 40 min, and more preferably 10 to 20 min. If the crosslinking reaction time is shorter than 1 min, the crosslinking reaction may not sufficiently occur. On the other hand, if the crosslinking reaction time is longer than 60 min, the properties of the superabsorbent polymer may deteriorate due to the excessive surface crosslinking reaction, and the polymer may be subjected to attrition because it spends a long time in the reactor.

A better understanding of the present invention may be obtained via the following examples, which are set forth to illustrate, but are not to be construed as limiting the scope of the present invention. The scope of the present invention is given by the claims, and also contains all modifications within the meaning and range equivalent to the claims. Unless otherwise mentioned, "%" and "part", indicating amounts in the following examples and comparative examples, are given on a mass basis.

MODE FOR INVENTION

Examples

Preparation Example: Preparation of Hydrous Gel Polymer 100 g of acrylic acid, 0.3 g of polyethyleneglycol diacrylate as a crosslinking agent, 0.033 g of diphenyl(2,4,6-trimethylbenzoyl)-phosphine oxide as an initiator, 38.9 g of sodium hydroxide (NaOH), and 103.9 g of water were mixed, thus preparing a monomer mixture.

Subsequently, the monomer mixture was placed on a continuously moving conveyor belt and irradiated with UV light (at a dose of 2 mW/cm$^2$) so that UV polymerization was carried out for 2 min, thus obtaining a hydrous gel polymer.

Example: Preparation of Superabsorbent Polymer

Example 1

The hydrous gel polymer obtained in the above preparation example was cut to a size of 5×5 mm, dried in a hot air oven at 170° C. for 2 hr, ground using a pin mill, and then sorted using a sieve, thereby obtaining a superabsorbent polymer having a particle size of 150 to 850 μm. 250 g of the superabsorbent polymer was mixed with 0.15 g of silica Aerogel (AeroZel™, JIOS) as porous superhydrophobic microparticles at 1000 RPM for 60 sec, added with a liquid mixture comprising 0.75 g of ethylene carbonate as a surface crosslinking agent and 6.75 g of water, and then mixed for 60 sec. Subsequently, the resulting mixture was reacted at 190° C. for 60 min, thus obtaining an unground superabsorbent polymer. The particle size of the unground superabsorbent polymer before grinding was measured, and the unground superabsorbent polymer was ground using a pin mill and then sorted using a sieve, yielding a superabsorbent polymer having a particle size of 150 to 850 μm. The Aerogel used had a particle size of 30 nm, a BET specific surface area of 500 m$^2$/g, a water contact angle of 150°, and a porosity of 95%.

The particle size of the Aerogel was measured via laser diffraction using a HELOS (Helium-Neon Laser Optical System) based on ISO 13320. The BET specific surface area and porosity were measured using a BET analyzer. The water contact angle was measured using a contact angle analyzer (KRUSS DSA100), and was specifically determined in a manner in which double-sided tape was attached to a flat glass plate, microparticles were applied in a monolayer thereon, and then 5 μL of ultrapure water was placed in the form of drop on the monolayer, and the angle between the water drop and the glass plate was measured four times and averaged.

Example 2

A superabsorbent polymer was obtained in the same manner as in Example 1, with the exception that silica Aerogel was used in an amount of 0.25 g.

Example 3

A superabsorbent polymer was obtained in the same manner as in Example 1, with the exception that the water in the liquid mixture was used in an amount of 11.75 g.

Example 4

A superabsorbent polymer was obtained in the same manner as in Example 1, with the exception that silica Aerogel was used in an amount of 0.25 g, and the water in the liquid mixture was used in an amount of 11.75 g.

Comparative Example 1

A superabsorbent polymer was obtained in the same manner as in Example 1, with the exception that REOLOSIL DM-30S was used as the microparticles. The REOLOSIL DM-30S that was used had a particle size of 7 nm, a BET specific surface area of 230 m$^2$/g, a water contact angle of 135°, and a porosity of 20% or less, and the measurement methods were the same as in Example 1.

Comparative Example 2

A superabsorbent polymer was obtained in the same manner as in Comparative Example 1, with the exception that 0.25 g of REOLOSIL DM-30S was used as the microparticles.

Comparative Example 3

A superabsorbent polymer was obtained in the same manner as in Comparative Example 1, with the exception that REOLOSIL DM-30S was used as the microparticles, and the water in the liquid mixture was used in an amount of 11.75 g.

Comparative Example 4

A superabsorbent polymer was obtained in the same manner as in Comparative Example 1, with the exception that 0.25 g of REOLOSIL DM-30S was used as the microparticles, and the water in the liquid mixture was used in an amount of 11.75 g.

Comparative Example 5

A superabsorbent polymer was obtained in the same manner as in Example 1, with the exception that the microparticles were not used.

Comparative Example 6

A superabsorbent polymer was obtained in the same manner as in Comparative Example 5, with the exception that the water in the liquid mixture was used in an amount of 11.75 g.

The features of Examples 1 to 4 and Comparative Examples 1 to 6 are shown in Table 1 below.

Table 1

| Kind of particles | | Liquid mixture | | |
|---|---|---|---|---|
| | | Amount of particles (g) | Ethylene carbonate (g) | Water (g) |
| Ex. 1 | Aerogel | 0.15 | 0.75 | 6.75 |
| Ex. 2 | | 0.25 | | 6.75 |
| Ex. 3 | | 0.15 | | 11.75 |
| Ex. 4 | | 0.25 | | 11.75 |
| C. Ex. 1 | REOLOSIL DM-30 S | 0.15 | | 6.75 |
| C. Ex. 2 | | 0.25 | | 6.75 |
| C. Ex. 3 | | 0.15 | | 11.75 |
| C. Ex. 4 | | 0.25 | | 11.75 |
| C. Ex. 5 | — | — | | 6.75 |
| C. Ex. 6 | | | | 11.75 |

Test Example

Evaluation of Properties

In order to evaluate the properties of the superabsorbent polymers of Comparative Examples 1 to 6 and Examples 1 to 4, the following tests were performed.

Test Example 1

Centrifugal Retention Capacity (CRC)

The superabsorbent polymers of Comparative Examples 1 to 6 and Examples 1 to 4 were measured for CRC. CRC was measured using the EDANA method WSP 241.3. Specifically, 0.2 g of a sample of the prepared superabsorbent polymer, pre-sorted or having a particle size of 150 to 850 µm, was placed in a teabag and then immersed in a 0.9% saline solution for 30 min. Thereafter, dehydration was performed for 3 min using centrifugal force equivalent to 250 G (gravity), and the amount of absorbed saline solution was measured.

Test Example 2

Absorption Under Pressure (AUP)

The superabsorbent polymers of Comparative Examples 1 to 6 and Examples 1 to 4 were measured for AUP. AUP was measured using the EDANA method WSP 242.3. Specifically, 0.9 g of a sample of the prepared superabsorbent polymer, pre-sorted or having a particle size of 150 to 850 µm, was placed in a cylinder according to the EDATA method, and a pressure of 0.7 psi was applied using a piston and a weight, after which the amount of 0.9% saline solution that was absorbed in 60 min was measured.

Test Example 3

Particle Size of Unground Superabsorbent Polymer

The unground superabsorbent polymers of Comparative Examples 1 to 6 and Examples 1 to 4 were measured for particle size. The particle size of the superabsorbent polymer was measured using the EDANA method WSP 220.3. 100 g of the superabsorbent polymer was sorted at 850 µm, 600 µm, 300 µm, and 150 µm using a mesh from Pan, and vibrated for 10 min under conditions of an amplitude of 1.44 mm and a vibration frequency of 50 Hz, and the amount remaining on each sieve was measured.

The results of measurement of CRC, AUP and particle size of the unground superabsorbent polymer in Test Examples 1 to 3 are shown in Table 2 below.

TABLE 2

| | CRC (g/g) | AUP (g/g) | Particle size (%) | | | | |
|---|---|---|---|---|---|---|---|
| | | | 150 µm or less | 150 to 300 µm | 300 to 600 µm | 600 to 850 µm | 850 µm or more |
| Ex. 1 | 33.9 | 20.3 | 0.0 | 2.3 | 28.3 | 43.9 | 25.5 |
| Ex. 2 | 33.1 | 19.5 | 0.7 | 11.3 | 52.5 | 31.4 | 4.1 |
| Ex. 3 | 33.3 | 22.1 | 0.0 | 0.6 | 11.2 | 20.2 | 68.0 |
| Ex. 4 | 31.1 | 20.0 | 0.0 | 1.0 | 29.3 | 38.7 | 31.0 |
| C. Ex. 1 | 33.7 | 21.3 | 0.2 | 2.3 | 19.8 | 29.0 | 48.7 |
| C. Ex. 2 | 34.5 | 19.6 | 0.5 | 8.4 | 46.2 | 36.2 | 8.7 |
| C. Ex. 3 | 32.2 | 22.7 | 0.0 | 0.4 | 5.2 | 7.3 | 87.1 |
| C. Ex. 4 | 32.3 | 21.5 | 0.0 | 0.5 | 5.6 | 8.5 | 85.4 |
| C. Ex. 5 | 34.1 | 23.8 | 0.0 | 1.7 | 15.5 | 27.7 | 55.1 |
| C. Ex. 6 | 32.7 | 24.0 | 0.0 | 0.9 | 6.0 | 10.9 | 82.2 |

As is apparent from the results of Table 2, the superabsorbent polymers having the superhydrophobic microparticles introduced to the surface thereof were decreased in agglomeration with an increase in surface hydrophobicity, consequently increasing processability.

Typically, a superabsorbent polymer is surface-crosslinked in a manner in which a surface crosslinking agent is dissolved in water and is then mixed with the superabsorbent polymer, thereby inducing uniform distribution and penetration on the surface of the superabsorbent polymer. As such, the use of water may increase the stickiness of the surface of the superabsorbent polymer, undesirably causing agglomeration. Grinding the agglomerated superabsorbent polymer requires a strong force, undesirably damaging the superabsorbent polymer.

The superabsorbent polymer modified with hydrophobicity by the addition of superhydrophobic particles in Example 1 exhibited smaller particle size distribution than the superabsorbent polymer of Comparative Example 5. The particle size of 850 µm or less was maintained at the level of about 75% even without the grinding process, from which the processability was evaluated to be improved.

Also, Example 1 and Comparative Example 1 show changes in processability due to the difference in hydrophobicity of the introduced superhydrophobic microparticles. When the superhydrophobic microparticles were used in the same amount, the particle size was decreased due to low agglomeration with an increase in the hydrophobicity, and particularly, the superabsorbent polymers of Examples 1 to 4 using the microparticles having higher hydrophobicity exhibited smaller particle size distribution than the superabsorbent polymers of Comparative Examples 1 to 4, and similar CRC and AUP values were manifested.

The invention claimed is:
1. A method of preparing a superabsorbent polymer, comprising:
    a) subjecting a monomer composition comprising a water-soluble ethylenic unsaturated monomer and a polymerization initiator to thermal polymerization or photopolymerization, thus preparing a hydrous gel polymer;

b) drying the hydrous gel polymer;
c) grinding the dried hydrous gel polymer;
d) adding particles having i) a BET specific surface area of 300 to 1500 $m^2/g$ and ii) a porosity of 50% or more and a surface crosslinking agent to the ground and dried hydrous gel polymer; and
e) after the adding of the particles and the surface crosslinking agent, performing a surface crosslinking reaction.

2. The method of claim 1, wherein the particles have a particle size ranging from 2 nm to 50 μm.

3. The method of claim 1, wherein the particles have superhydrophobicity with a water contact angle of 125° or more.

4. The method of claim 1, wherein the particles have a particle size ranging from 2 nm to 50 μm and superhydrophobicity with a water contact angle of 125° or more.

5. The method of claim 1, wherein the particles have a BET specific surface area of 500 to 1500 $m^2/g$.

6. The method of claim 3, wherein the particles have superhydrophobicity with a water contact angle of 140° or more.

7. The method of claim 3, wherein the particles have superhydrophobicity with a water contact angle of 145° or more.

8. The method of claim 1, wherein the particles have a porosity of 90% or more.

9. The method of claim 1, wherein the particles are used in an amount of 0.001 to 1 parts by weight based on 100 parts by weight of the superabsorbent polymer.

10. The method of claim 1, wherein the particles comprise at least one selected from the group consisting of silica, alumina, carbon, and titania ($TiO_2$).

11. The method of claim 1, further comprising grinding the hydrous gel polymer to a particle size ranging from 1 to 15 mm, before the drying in b).

12. The method of claim 1, wherein the drying in b) is performed at a temperature ranging from 150 to 250° C.

13. The method of claim 1, wherein the grinding in c) comprises grinding the hydrous gel polymer to a particle size ranging from 150 to 850 μm.

14. The method of claim 1, wherein the surface crosslinking agent in d) comprises any one or more selected from the group consisting of a polyhydric alcohol compound, an epoxy compound, a polyamine compound, a haloepoxy compound, a haloepoxy compound condensed product, an oxazoline compound, a mono-, di- or poly-oxazolidinone compound, a cyclic urea compound, a polyhydric metal salt, and an alkylene carbonate compound.

15. The method of claim 1, wherein the surface crosslinking agent in d) is added in an amount of 0.001 to 5 parts by weight based on 100 parts by weight of the ground polymer.

16. The method of claim 1, wherein the surface crosslinking agent in d) is added under a condition that a surface temperature of the polymer is 60 to 90° C.

17. The method of claim 1, wherein the surface crosslinking agent in d) has a temperature ranging from 5 to 40° C.

18. The method of claim 1, wherein the surface crosslinking reaction in e) is carried out for 10 to 120 min.

19. The method of claim 1, wherein e) is performed through heating by applying any one or more selected from the group of heat sources including steam, electricity, UV light, and IR light.

20. The method of claim 1, further comprising grinding the superabsorbent polymer to a particle size ranging from 150 to 850 μm, after the performing the surface crosslinking reaction in e).

21. The method of claim 4 wherein the particles have superhydrophobicity with a water contact angle of 140° or more.

22. The method of claim 4 wherein the particles have superhydrophobicity with a water contact angle of 145° or more.

* * * * *